United States Patent [19]

Eriksson et al.

[11] Patent Number: 6,083,707
[45] Date of Patent: Jul. 4, 2000

[54] THYMIDINE KINASE TK1, PEPTIDE, CORRESPONDING ANTIBODIES AND USE OF THESE IN DETERMINATION OF TUMOR PROLIFERATION

[76] Inventors: Staffan Eriksson, Pilvägen 2, S-181 57 Lidingö; Sven Skog, Herrårdsvägen 15, S-194 35 Upplands Väsby; Bernhard Tribukait, Furulund, S-178 93 Drottningholm, all of Sweden

[21] Appl. No.: 08/732,393

[22] PCT Filed: Apr. 21, 1995

[86] PCT No.: PCT/SE95/00435

§ 371 Date: Oct. 22, 1996

§ 102(e) Date: Oct. 22, 1996

[87] PCT Pub. No.: WO95/29192

PCT Pub. Date: Nov. 2, 1995

[30] Foreign Application Priority Data

Apr. 22, 1994 [SE] Sweden .................................. 9401380

[51] Int. Cl.[7] ...................... G01N 33/573; G01N 33/563; C07K 7/08; C07K 16/40
[52] U.S. Cl. ........................... 435/7.4; 435/7.2; 435/7.23; 435/975; 435/183; 435/194; 436/512; 436/536; 436/547; 436/813; 436/387.7; 436/388.26; 436/388.8; 436/388.853; 436/389.7; 436/391.1; 436/391.3; 436/395; 436/866
[58] Field of Search ..................................... 435/7.2, 7.23, 435/975, 183, 194, 7.4; 436/512, 536, 547, 813; 530/300, 326, 350, 387.1, 387.7, 388.26, 388.8, 388.85, 389.7, 391.1, 391.3, 395, 866

[56] References Cited

U.S. PATENT DOCUMENTS 4,317,877  3/1982  Balis et al. .............................. 435/7.23

FOREIGN PATENT DOCUMENTS 0255431  2/1988  European Pat. Off. .
9504758  2/1995  WIPO .

OTHER PUBLICATIONS

Kauffman et al., Molec. and Cell. Biol., 11:2538–46, 1991.

Bradshaw et al., Mol. Cell. Biol., vol. 4:2316–2320, 1984.

Dialog Information Services, (1994) File 159, No. 01073620, *Proc.Annu.Am.Assoc.Cancer Res*; 35:A1200.

*Primary Examiner*—Ronald B. Schwadron
*Attorney, Agent, or Firm*—Birch, Stewart, Kolasch & Birch, LLP

[57] ABSTRACT

The invention discloses the use of a new cell growth related peptide. More precisely, the invention serves as a marker for cell proliferation. The marker is a peptide which is an exposed part of a cellular enzyme. This peptide is as well particularly useful as an aid in production of highly selective reactive molecules. The peptide is a part of thymidine kinase TK1 and has the sequence of SEQ ID NO: 1 or SEQ ID NO: 2.

10 Claims, 5 Drawing Sheets

(3 of 5 Drawing Sheet(s) Filed in Color)

SEQUENCE LISTING (1) GENERAL INFORMATION:

(iii) NUMBER OF SEQUENCES: 2

(2) INFORMATION FOR SEQ ID NO:1:

```
        (i) SEQUENCE CHARACTERISTICS:
            (A) LENGTH: 15 amino acids
            (B) TYPE: amino acid
            (C) STRANDEDNESS: single
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (ix) FEATURE:
            (A) NAME/KEY: Modified-site
            (B) LOCATION: 1..2
            (D) OTHER INFORMATION: /product= "OTHER"
                /label= Modified-Site
                /note= "The Xaa in the 1 position is Acetyl-Lysine"

(xi) SEQUENCE DESCRIPTION: SEQ ID NO:1:

Xaa Pro Gly Glu Ala Val Ala Ala Arg Lys Leu Phe Ala Pro Gln
1               5                   10                  15

(2) INFORMATION FOR SEQ ID NO:2:

(i) SEQUENCE CHARACTERISTICS:
            (A) LENGTH: 15 amino acids
            (B) TYPE: amino acid
            (C) STRANDEDNESS: single
            (D) TOPOLOGY: Not Relevant (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:2:

Lys Pro Gly Glu Ala Val Ala Ala Arg Lys Leu Phe Ala Pro Gln
1               5                   10                  15
```

THYMIDINE KINASE TK1, PEPTIDE, CORRESPONDING ANTIBODIES AND USE OF THESE IN DETERMINATION OF TUMOR PROLIFERATION

This application is a 371 of PCT/SE95/00435 filed Apr. 21, 1995.

TECHNICAL FIELD

The present invention concerns a new cell growth related peptide and use thereof. More precisely, the invention serves as a marker for cell proliferation and this marker is a specific peptide sequence which is a part of the cellular enzyme thymidine kinase. This peptide can be used as an immunogen for antibody production or used by other techniques to obtain molecules that react with the peptide. The antibodies or the reactive molecules can be used for determination of the degree of proliferation of tumors or other tissues from human and animals.

BACKGROUND

In respect to clinical investigations, the proportion of DNA-synthesizing cells (S-phase cells) in tumors has been used as a measure of their proliferation rate. The DNA-synthesizing cells have earlier been determined by means of radioactive labelled thymidine (autoradiography). Recently, even incorporation of halogene-analogs of thymidine (BrdU) and antibodies against these have been used and, to a large extent, quantitative flowcytometric DNA measurements. The disadvantage with the use of isotopic labelled thymidine and BrdU is the fact that only living cells can be measured. Therefore, these methods have only been used on selected patients and in a limited number of studies (1). Flow-cytometry, a technique working with fixed non-living cells, but also with stored cell material, has high capacity, but is unable to distinguish between proliferating and non-proliferating S-phase cells. Determination of S-phase cells is even more complicated in tumors containing both normal and malignant cells which do not deviate in their DNA-content from benign cells (2). Other methods for determination of markers specifically related to proliferating cells are known. For example, Ki-67 and PCNA (3). Ki-67 is a monoclonal antibody against a substance in the cell nucleus. The exact nature of Ki-67 is still unknown. Ki-67 is expressed in all cell cycle stages except in $G_o$ and early $G_1$, with a maximum in $G_2$ and mitosis. One type of antibody available on the market can only be used in fresh tissues, one newer type also in formalin fixed, paraffine embedded tissues.

PCNA is a nuclear protein (36 kD) identical with that of the subunit of DNA-polymerase delta. Depending on the cell proliferation rate, PCNA is expressed in all cell cycle stages. PCNA is not as sensitive for various fixation techniques as Ki-67 (3).

A problem with Ki-67 and PCNA is that these substances are expressed in all cell cycle stages and thus only to some extent reflected the proportion of S-phase cells.

Thymidine kinases appear in two different forms, a cytoplasmic (TK1) (4) and a mitochondrial (TK2) (5) form, with different genetic origin. TK1, which can be subdivided into different variants (6), is closely related to cell proliferation and starts to be synthesized at the border of $G_1/S$ (7). TK1 is degraded in connection with mitosis (8). Thus, TK1 is a specific marker for S and $G_2$ cells.

There have been several attempts to make TK1 specific antibodies with the intact protein and various recombinant forms. However, due to the fact that the primary structure of TK1 is highly conserved between different species there are very few antibodies reported and the antibodies produced show extensive cross reactivity to other proteins (8, 9).

EP A1 255 431 describes a foetal form of thymidine kinase (TK-F) which is said to have a superior enzymatic activity compared to previously known TK-F. Moreover, the applicant describes a purification procedure and use of TK-F to produce antibodies. These antibodies are said to have a surprising effect on patients with hormone dependent cancer, especially prostate and breast cancer, respectively. Diagnostic use of said antibodies is solely mentioned and the application describes nothing further in this respect.

EP A2 137 492 describes a process for early diagnosing of malignant tumors with antibodies directed against different blood forms of nucleoside-nucleotide phosphotransferases. Here not only thymidine kinase is determined but also several other phosphotransferases which means that the process is not specific for thymidine kinase.

The present invention makes it possible to estimate the proportion of proliferating S and $G_2$ cells by determining the cellular concentration of the cytosolic thymidine kinase. This determination is enabled by using antibodies against a defined part of TK 1, namely a 15 amino acid residues peptide. The antibodies according to the invention do not produce any cross reactivity with other proteins.

The peptide sequence according to the invention represents a unique structure at the C-terminal end of the protein which is most likely part of an external bend region of the protein. It is also known that C-terminal sequences are involved in cell cycle specific degradation of TK1 (8). Therefore, this amino acid sequence is most likely specifically immunogenic and the corresponding epitope of TK1 is exposed and present only in intact TK1.

Measurements of TK1 activity in serum of patients with malignancies have been extensively used as a marker of disease (10). However the TK1 activity determinations by radioactive substrate assay is relatively complex. Therefore, there is a need for simplified quantitative assays for TK1 that could be used in cell extracts, cells, tissues and body fluids.

This need is fulfilled according to the invention by antibodies that are unique and can serve as specific markers for proliferating cells, since the antigen is expressed only in S and $G_2$ cells. These antibodies can be used to determine the degree of proliferation in any tumor and the antibodies have been used with both fresh and stored paraffine embedded cell material. The antibodies can react with TK1 also after various types of fixation.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The invention will now further be described in detail with reference to FIGS. 1A–5.

PRODUCTION AND CHARACTERIZATION OF THE POLYCLONAL TK1 ANTISERUM

In order to produce a polyclonal rabbit-antiserum specific for TK1, rabbits were immunized and boostered with the following synthetic 15 amino acid peptide (SEQ ID. NO: 1) according to the invention from the C-terminus part of TK1 (11). The Acetyl group on the N-terminal Lysine is optional.

Acetyl-Lys-Pro-Gly-Glu-Ala-Val-Ala- (SEQ ID NO:1)
Ala-Arg-Lys-Leu-Phe-Ala-Pro-Gln The sequence lacking the Acetyl group is SEQ ID NO: 2.

Amino acids 210 to 224 from the C-terminal part of the TK1 cDNA-sequence (ref. 4).

Figure 1A:
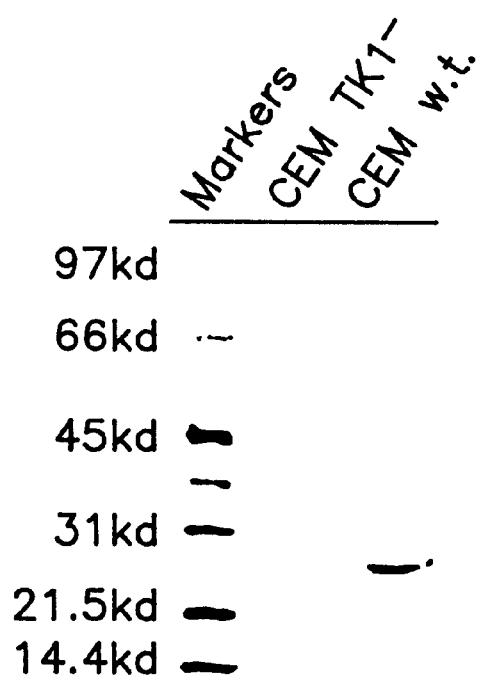
FIGS. 1A and B show Western immunoblotting with extracts using TK1 antibodies.
Figure 1B:
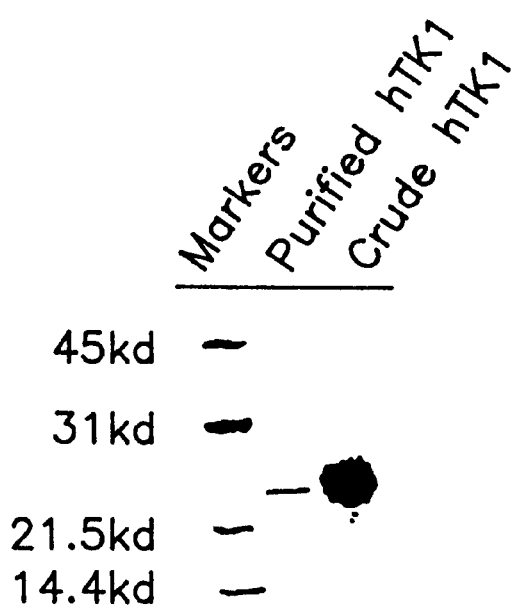
Figure 2A:
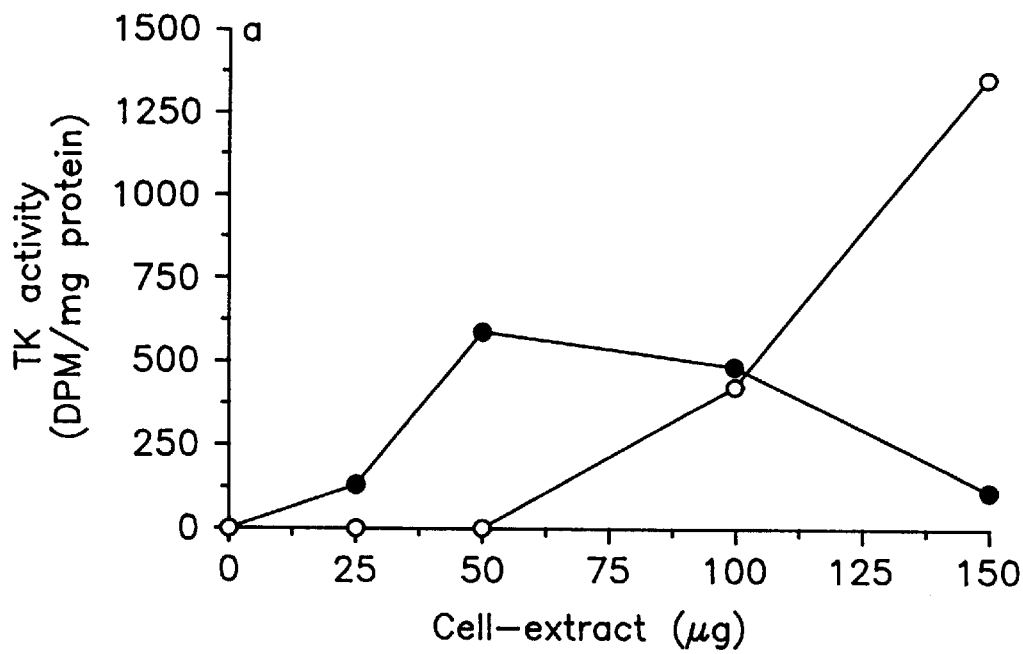
FIGS. 2A and B show inhibition of TK1 activity in cell extracts after immunoprecipitation with the peptide antibody.
Figure 2B:
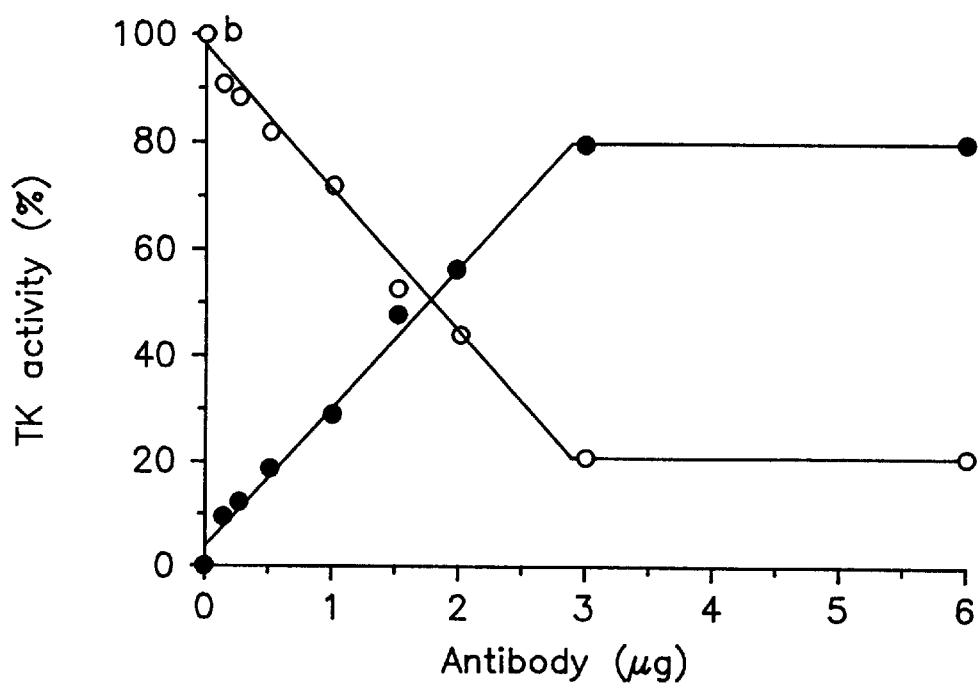
Figure 3A:
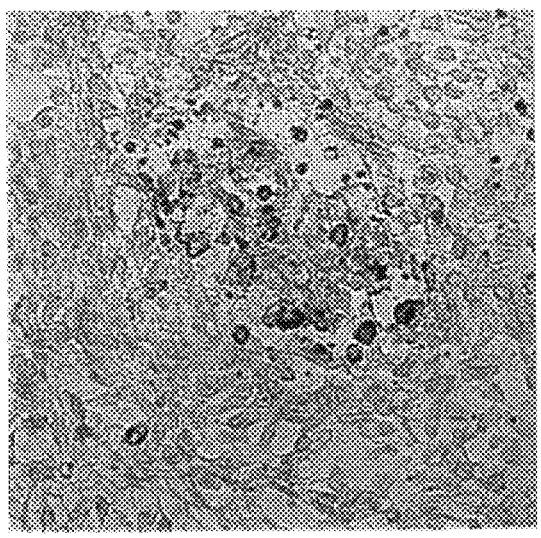
FIG. 3A shows examples of an immunostained formalin fixed and paraffin embedded embryonal carcinoma and a prostate-carcinoma, respectively.
Figure 3B:
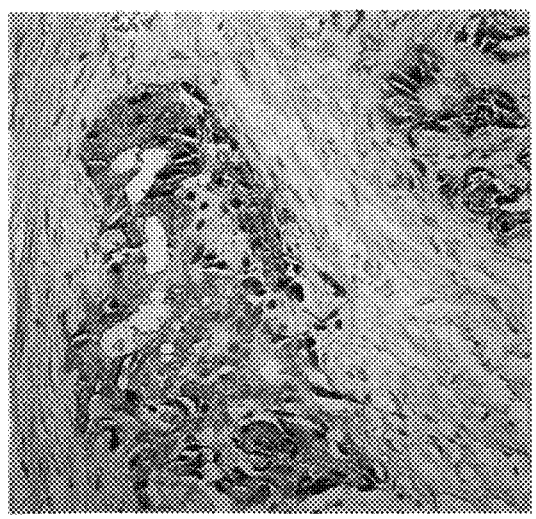
FIG. 3B shows immunostained teratocarcinoma from a patient; intestinal-like component and osteal component, respectively.
Figure 4A:
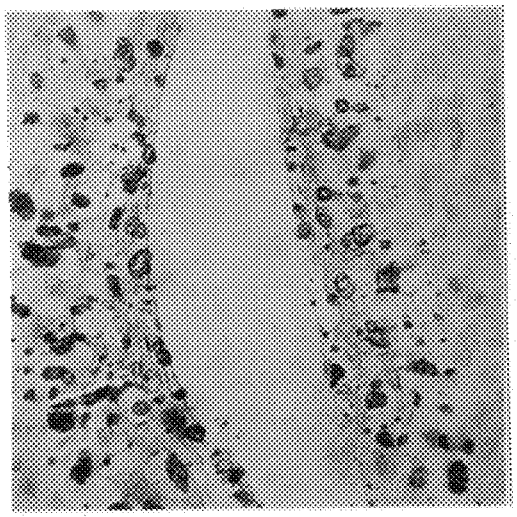
FIGS. 4A and B shows immunostaining of HeLa-cells (ABC-AP).
Figure 4B:
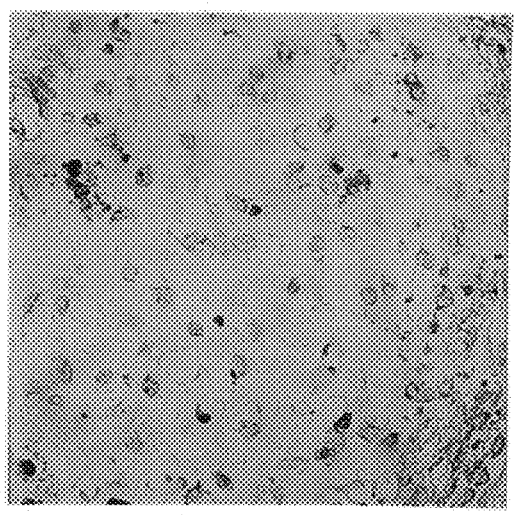

This sequence of TK1 is believed to be located on the surface of the TK1 protein and does not show any sequence homology with other known proteins. The peptide was linked to a carrier protein to produce a stronger immunoreactivity in the rabbit. Rabbits were injected with 100–200 μg of the peptide one to three times per week and the serum was then collected after two to four weeks. The antiserum was precipitated with 40% ammoniumsulfate. The antibodies were purified by desalting on a SEPHADEX® G-25 column followed by affinity chromatography on a peptide-Sephadex column and as a result, about 5 mg purified antibody could be obtained from approximately 50 ml serum. The specificity of the antibodies was tested with purified TK 1, cell extract from human lymphoid tumor cells, stimulated human lymphocytes, mouse ascites tumor cells and mouse lymphoma tumor cells by means of ELISA and Western immunoblotting techniques. As negative controls were used human lymphoid tumor cells lacking thymidine kinase 1, human peripheral unstimulated lymphocytes, and purified thymidine kinase 2 peptide from human liver. To identify TK1 in Western immunoblotting, a human TK1 peptide was used obtained from transfected E. coli. After purification of the antibodies, no immunoreactivity was observed with the negative controls (FIGS. 1A and B). In addition, no immunoreactivity was found against deoxycytidine kinase (dCK), an enzyme, like TK1, involved in DNA synthesis. The immunoresponse of the TK1 antibodies was in addition determined in cell extract by immunoprecipitation. After immunoprecipitation, the enzyme activity was determined in both the supernatant and the pellet-fractions (FIGS. 2A and B). The results show a specific binding of the antibodies to TK1, but also that the binding did not inhibit the TK1 activity. The antibodies were also used for immunostaining of intact fixed CEM and EAT cells (peroxidase, fluorescence). As negative controls, unstimulated human lymphocytes and CEM TK-negative cells were used. These cells showed no staining (FIGS. 1A and B). The results demonstrated that the cytoplasm, but not the nucleus, was immunostained, which speaks in favor of that TK1 is produced only in the cytoplasm of the cell. In summary, the peptide antibodies react specifically with TK1 in extracts or in cells and can therefore be used as reagents to determine cellproliferation. Except for the production of polyclonal antibodies, the present invention also includes production of monoclonal antibodies against the same synthetic 15 amino acid peptide or be used by other known molecular genetic methods, such as the phage technique, to obtain reactive molecules with specific binding to the same peptide.

Since the antibodies react specifically with TK1 in extract from proliferating cells it can be used to determine the TK1 levels by different immunotechniques in tissues, cells and body fluids. For use in immunoassays, the antibodies according to the invention can be intact or fragmented as common in the state of the art.

CORRELATION BETWEEN CELLULAR CONCENTRATION OF TK1 IN CELLS, CELL EXTRACTS AND ITS ENZYMATIC ACTIVITY

In order to determine the relationship between the cellular concentration of TK1 in extracts and its activity and thus be able to use the TK1 antibodies for determination of the degree of proliferation in tumors, a number of experiments were carried out with human CEM and HeLa cells and mouse EAT cells isolated from various parts of the cell cycle ($G_1$, S and $G_2$/M). TK-activity is low in $G_1$, increases in S-phase and remains high or decreases in $G_2$. Cells from the various parts of the cell cycle were obtained by elutriation centrifugation. The cellular concentration of TK1 in extracts was determined by Western immunoblotting and ELISA, as well as by means of immunostaining of these cells. A close correlation between TK-activity and the extent of immunoreactivity was found in extracts from all three cell lines. The immunostaining of the intact cells correlates closely to TK1-activity. The same type of results was obtained with activated peripheral blood lymphocytes from HIV-positive and negative individuals, using the same antibodies (12).

In conclusion, the TK1 antibodies, according to the invention, reacted with S and $G_2$ cells and thus, can be used as reagents to determine cell proliferation.

DEGREE OF PROLIFERATION OF TUMORS AS DETERMINED BY TK1 ANTIBODIES

The applicability of the TK1 antibodies was further studied in different types of tumors (teratocarcinoma, embryocarcinoma, adenocarcinoma from prostate). Tumor cells fixed in formalin and embedded in paraffin according to normal procedures, were stained with peptide antibodies and visualized by the help of secondary antibodies with ABC-HRP, ABC-AP or avidin labelled Texas red. The results show that tumor cells were positive while the surrounding tissue of normal cells were negative (FIGS. 3A–B and 4A–B). Similar results were also obtained in samples from human leukemia.

Figure 5:
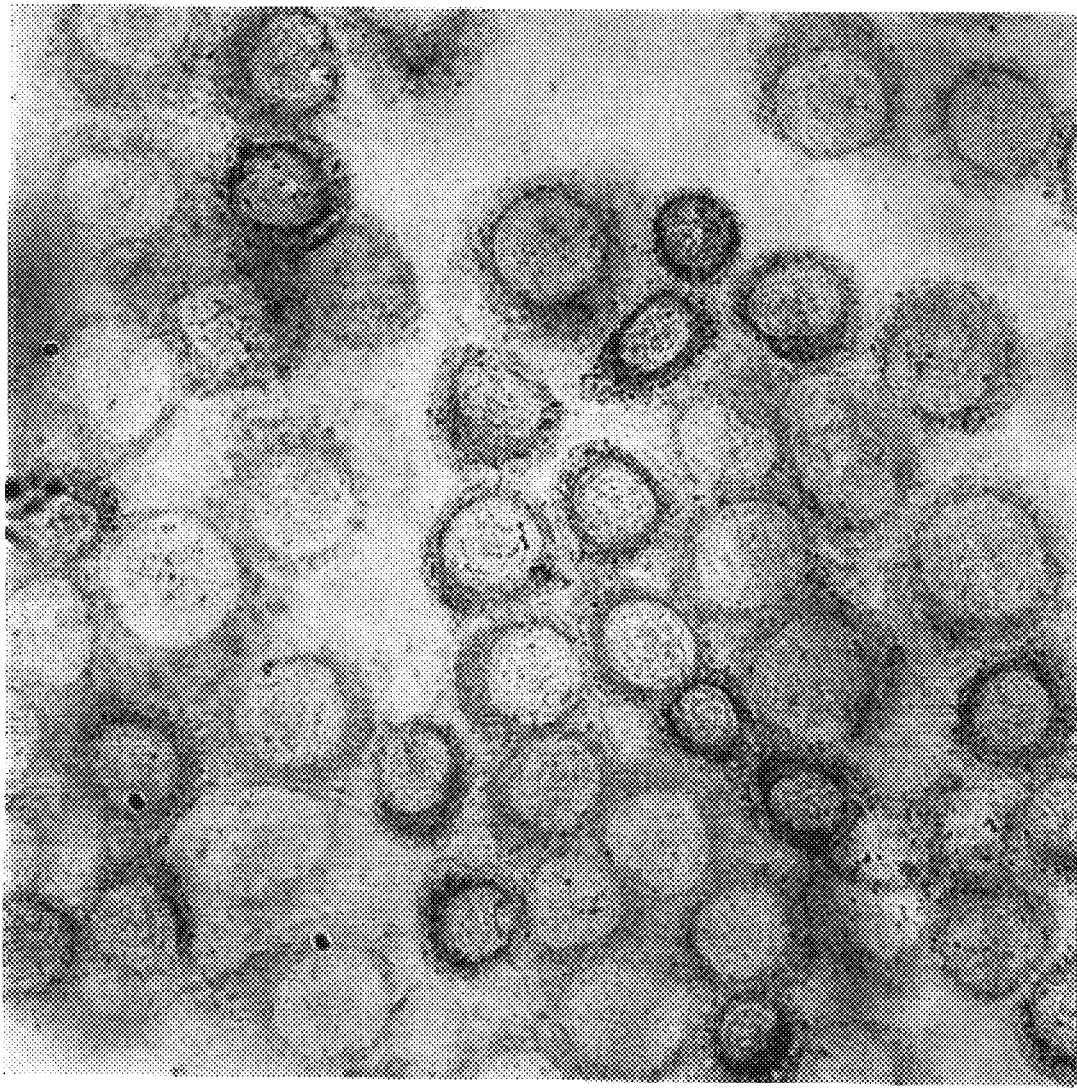
FIG. 5 shows studies with HeLa cells showing staining of the cytoplasm, but not the nucleus.

Studies with human tumor cells (HeLa) cells show staining of the cytoplasm, but not of the nucleus (FIG. 5).

In order to determine the relationship between the proportion of positive cells and the proportion of $S+G_2$-cells, the immunoreactivity and the position in the cell cycle were determined in individual cells by means of single cell imaging and flow cytometry in four different cell types (Table 1). A close correlation between the proportion of positive cells and cells in $S+G_2$ was found as shown in the table.

TABLE 1

| Cell type | % positive cells (> 400 cells) | % S + $G_2$ |
|---|---|---|
| CEM | 39.0 | 33.3 |
| EAT | 33.6 | 44.0 |
| HeLa | 42.8 | 36.5 |
| Stim. Lymph. | 28.7 | 19.8 |

To further study the correlation between TK1 positive cells and the proportion of $S+G_2$ cells, human tumor cells (CEM, HeLa) were isolated from various parts of the cell cycle by elutriation. Fractions of cells with different percentage of $S+G_2$ cells were obtained. A close correlation (0.91) between TK1 positive cells and proportion of $S+G_2$ was found.

The immunoresponse of the TK1 antiserum with normal proliferating cells and the unspecific binding of the antibodies with non-proliferating differentiated cells were studied in different mouse tissues (Table 2). Such investigations are of importance to determine if the antiserum is useful for clinical studies.

TABLE 2

| Cell types | Staining |
|---|---|
| Stomach | |
| Epithelial cells | − |
| Glandular cells | + |
| Parietal cells | +/− |
| Liver | |
| Hepatocytes | − |
| Kidney | |
| Tubular cells | − |
| Glomelurar cells | − |
| Testis | |
| Primary spermatocytes | − |
| Secondary spermatocytes | + |
| Sperm cells | − |

The results of this study show that only proliferating cells, such as secondary spermatocytes and glandular cells, are TK1 positive, while differentiated cells are negative.

PROLIFERATION OF STIMULATED LYMPHOCYTES FROM HIV INFECTED PATIENTS AS DETERMINED WITH TK1 ANTIBODIES

Azidothymidine (AZT) is a drug used for treatment of HIV infected patients. AZT is blocking the reverse transcriptase enzyme of the HIV-virus. AZT is activated by TK1 to AZT monophosphate in infected cells. In a study of 49 HIV infected patients, TK1 activity in mitogen stimulated lymphocytes from these patients was determined (12). As controls, lymphocytes from 20 healthy volunteers were used. The knowledge about the TK activity in such patients is important to evaluate the result of chemotherapy treatment. To exclude that the variations in TK activity was due to methodological difficulties, the cellular concentration of TK1 in extracts was determined by Western immunoblotting using the polyclonal TK1 antibody, according to the invention. A close correlation between TK1 activity and the cellular concentration of TK1 was obtained (12). Thus, in this cell system, the cellular concentration of TK1 reflected to a high degree the proliferation of these cells.

ANALYTIC USE OF TK1 ANTIBODIES ACCORDING TO THE INVENTION

The invention also relates to antibodies in kits to perform 1 site or 2 sites immunoassays.

In kits for 2 sites immunoassays there is, besides the TK1 antibody described above, preferably also comprised an antibody having another specificity. For example, the other antibody is one produced against the whole TK1 protein or parts of it.

REFERENCES

1. Wilson, G. D.. Assessment of human tumour proliferation using bromodeoxyuridine—current status. Acta Oncol., 30:903–910, 1991.
2. Tribukait, B.. Flow cytometry in assessing the clinical aggressiveness of genito-urinary neoplasms. World J. Urol., 5:108–122, 1987.
3. Hall, P. A., Woods, A. L.. Immunohistochemical markers of cellular proliferation: achievements, problems and prospects. Cell Tissue Kinet. 23:505–522, 1990.
4. Bradshaw, H. D. Jr., Deininger, P. L.. Human thymidine kinase gene: Molecular cloning and nucleotide sequence of a cDNA expressible in mammalian cells. Mol. Cell Biol. 4: 2316–2320, 1984.
5. Munch-Petersen, B., Cloos, G., Tyrsted, G., Eriksson, S.. Divering substrate specificity of pure human thymidine kinase 1 and 2 against antiviral dideoxy nucleosides. J. Biol. Chem. 266: 2032–2038, 1991.
6. He, Q., Skog, S., Welander, I., Tribukait, B.. Enzyme kinetics of thymidine isoenzymes of Ehrlich ascites tumour cells. Anticancer Res. 10: 1257–1264, 1990.
7. He, Q., Skog, S., Tribukait, B.. Cell cycle related studies on thymidine kinase and its isoenzymes in Ehrlich ascites tumour cells. Cell Prolif. 24: 3–14, 1991.
8. Kauffman, M. G., Kelly, T. J. Cell cycle regulation of thymidine kinase: Residues near the carboxyl terminus are essential for the specific degradation of the enzyme at mitosis. Mol. Cell. Biol. 11: 2538–2546, 1991.
9. Hengstschläger, M., Knöfler, M., Müller, E. W., Ogris, E., Wintersberger, E., Wawra, E.. Different regulation of thymidine kinase during the cell cycle of normal versus DNA tumor virus-transformed cells. J. Biol. Chem. 269: 13836 13842, 1994.
10. Gronowitch, J. S., Hagberg, H., Källander, C. F. R., Simonsson, B.. The use of serum deoxythymidine kinase as a prognostic marker, and in the monitoring of patients with non-Hodgkin s lymphoma. Br. J. Cancer. 47: 487–495, 1983.
11. He, Q., Skog, S., Eriksson, Wang, N., Tribukait, B.. A peptide antibody against a C-terminal part of human and mouse cytosolic thymidine kinase is a marker for cell proliferation. Manuscript in preparation.
12. Jacobson, B., Britton, S., He., Q., Karlsson, A., Eriksson, S.. Thymidine kinase levels are decreased in activated blood mononuclear cells from HIV infected compared to not infected persons. In press Aids & Hum. Retrovir.

We claim:

1. A peptide consisting of the amino acid sequence according to SEQ ID NO: 1 or SEQ ID NO: 2.

2. An antibody produced against the peptide according to claim 1.

3. A fragment of an antibody produced against the peptide according to claim 1, wherein said fragment binds to said peptide.

4. A method for determining the thymidine kinase 1 activity of cells which comprises exposing cells to an antibody or fragment thereof according to claim 2 or 3; and detecting the amount of said antibody bound to thymidine kinase 1.

5. A method for determining the proliferation grade of tumors which comprises exposing tumor cells to an antibody according to claim 2; and detecting the amount of said antibody bound to thymidine kinase 1.

6. The method according to claim 4 wherein the determination is performed on tissues, cells or body fluids.

7. Kit comprising a first antibody according to claim 2 or a fragment thereof according to claim 3 to determine the proliferation grade of tumors.

8. Kit according to claim 7, further comprising a second antibody having a specificity different from said first antibody.

9. Kit according to claim 8, wherein the second antibody is produced against the whole thymidine kinase 1.

10. The method according to claim 5, wherein the determination is performed on tissues, cells or body fluids.

* * * * *